United States Patent [19]

Levy

[11] Patent Number: 5,586,132
[45] Date of Patent: Dec. 17, 1996

[54] METHOD AND APPARATUS FOR GENERATING BRIGHT LIGHT SOURCES

[75] Inventor: Uri Levy, Rehovot, Israel

[73] Assignee: Laser Industries Ltd., Tel Aviv, Israel

[21] Appl. No.: 280,939

[22] Filed: Jul. 27, 1994

[51] Int. Cl.$^6$ .................................................. H01S 3/25
[52] U.S. Cl. ............................. 372/23; 385/115; 606/3
[58] Field of Search ............................. 372/9, 20, 23, 372/24, 28, 108; 385/31, 47, 115–121, 901; 606/16–19, 3

[56] References Cited

U.S. PATENT DOCUMENTS

| | | | |
|---|---|---|---|
| Re. 33,722 | 10/1991 | Scifres et al. ........................ | 385/115 X |
| 3,590,248 | 6/1971 | Chatterton, Jr. ..................... | 385/115 X |
| 4,408,602 | 10/1983 | Nakajima ............................. | 606/16 X |
| 4,823,357 | 4/1989 | Casey .................................... | 372/20 X |
| 4,932,747 | 6/1990 | Russell et al. ....................... | 385/115 |
| 5,009,658 | 4/1991 | Damgaard-Iversen et al. ...... | 606/3 X |
| 5,139,494 | 8/1992 | Freiberg ................................ | 606/3 |
| 5,219,347 | 6/1993 | Negus et al. ......................... | 606/17 |
| 5,232,366 | 8/1993 | Levy ..................................... | 606/3 X |
| 5,290,274 | 3/1994 | Levy et al. ........................... | 606/3 X |
| 5,387,211 | 2/1995 | Saadatmanesh et al. ............ | 606/17 X |

*Primary Examiner*—John D. Lee
*Attorney, Agent, or Firm*—Cobrin Gittes & Samuel

[57] ABSTRACT

A method and apparatus for generating bright light sources includes a first plurality of semiconductor lasers in which each of the first plurality of semiconductor lasers emits a beam of light of a first frequency; a second plurality of semiconductor lasers in which each of the second plurality of semiconductor lasers emits a beam of light of a second frequency; a first bundle of optical fibers for receiving the light from ones of the first plurality of semiconductor lasers and providing a first combined laser beam of a predetermined shape and having a cross-sectional area and a solid angle; a second bundle of optical fibers for receiving the light from ones of the second plurality of semiconductor lasers and providing a second combined laser beam of a predetermined shape and having a cross-sectional area and a solid angle; and frequency responsive optics for combining the first and second combined laser beams into a composite laser beam, the composite laser beam having substantially the same product of cross-sectional area and solid angle as each of the first and second combined beams.

25 Claims, 1 Drawing Sheet

METHOD AND APPARATUS FOR GENERATING BRIGHT LIGHT SOURCES

FIELD OF THE INVENTION

The present invention relates generally to a method and apparatus for generating bright light sources and more particularly, to a method and apparatus for generating bright light sources using semiconductor lasers of different wavelengths to perform medical laser applications.

BACKGROUND OF THE INVENTION

In many applications, particularly medical laser applications, it is necessary to concentrate relatively high laser power onto a small area, e.g., for ablating or cutting tissue. This application of lasers requires that the laser source be of high brightness; that is, it must emit a high power beam of small area and small divergence. Brightness is directly proportional to the output power and inversely proportional to the source area and also to the solid angle of the light beam. (Brightness=power/(Source Area x Solid Angle)) It is therefore difficult to increase the brightness of a source by increasing the output power, since this also tends to increase the source area and/or the solid angle of the light beam such that the net effect on the brightness is relatively small. For example, suppose the object is to double the brightness of a particular laser that emits 1 watt of power into a certain solid angle. By simply taking another such laser and placing it adjacent the first, the result is two watts of power into essentially the same solid angle, but the total cross-sectional area of the new source is also twice as large such that the brightness of the combined source is essentially equal to the brightness of each separate laser (not double the brightness).

It has been proposed to use a plurality of laser diodes to provide a higher power laser diode light source from an optical fiber. An example of such a laser diode light source is disclosed in UK Patent Application GB 2256503A.

The prior art teaches to increase the brightness of a light source by using a polarized beam combiner on two beams of light of orthogonal polarizations from two laser diodes, thus combining the two beams into a single composite beam. The prior art further teaches to feed this composite beam into a fiber optic cable and then to bundle a group of these fiber optic cables to form a larger more powerful beam of light. This method suffers from a number of problems some of which include: the power output being limited by being able to combine only two laser diodes with each polarized beam combiner, and the multitude of polarized lasers and optics being very complex and expensive (this method requires a large number of beam combiner pairs to achieve a desired high power).

Thus there exists a need for a more efficient way to combine a plurality of laser diodes to form a relatively high brightness laser light source for performing medical laser applications.

It is thus an object of the present invention to provide a method of and an apparatus for generating a beam of bright light for medical laser applications.

It is another object of the present invention to provide a method of and an apparatus for generating a beam of bright light by efficiently combining a plurality of semiconductor lasers.

It is another object of the present invention to provide a method of and an apparatus for generating a beam of bright light by combining a plurality of semiconductor lasers of different frequencies.

It is yet another object of the present invention to provide a method of performing medical laser applications by generating a first laser beam of a first frequency, generating a second laser beam of a second frequency, combining the first and second laser beams into a composite laser beam then shining the composite laser beam into tissue.

Another object of the present invention is to provide an apparatus for generating a beam of bright light utilizing semiconductor lasers of different frequencies, bundles of optical fibers to form composite single frequency laser beams from the lasers of different frequencies respectively and frequency responsive optics for combining the composite laser beams of the different frequencies into a combined laser beam.

SUMMARY OF THE INVENTION

The foregoing objects are attained by the invention, which provides a method of and an apparatus for generating a bright light source including a first and a second plurality of semiconductor lasers in which each of the first and second plurality of semiconductor lasers respectively emits a beam of a first and second frequency. A first and a second bundle of optical fibers may respectively be used for receiving the light from ones of the first and second plurality of semiconductor lasers and for providing a first and a second combined laser beam of a predetermined shape and having a cross-sectional area and a solid angle. Frequency responsive optics are used for combining the first and second combined laser beams into a composite laser beam having substantially the same product of cross-sectional area and solid angle as each of the first and second combined beams.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and accompanying drawings in which.

DETAILED DESCRIPTION OF THE PREFERRED EMBODIMENT

Figure 1:
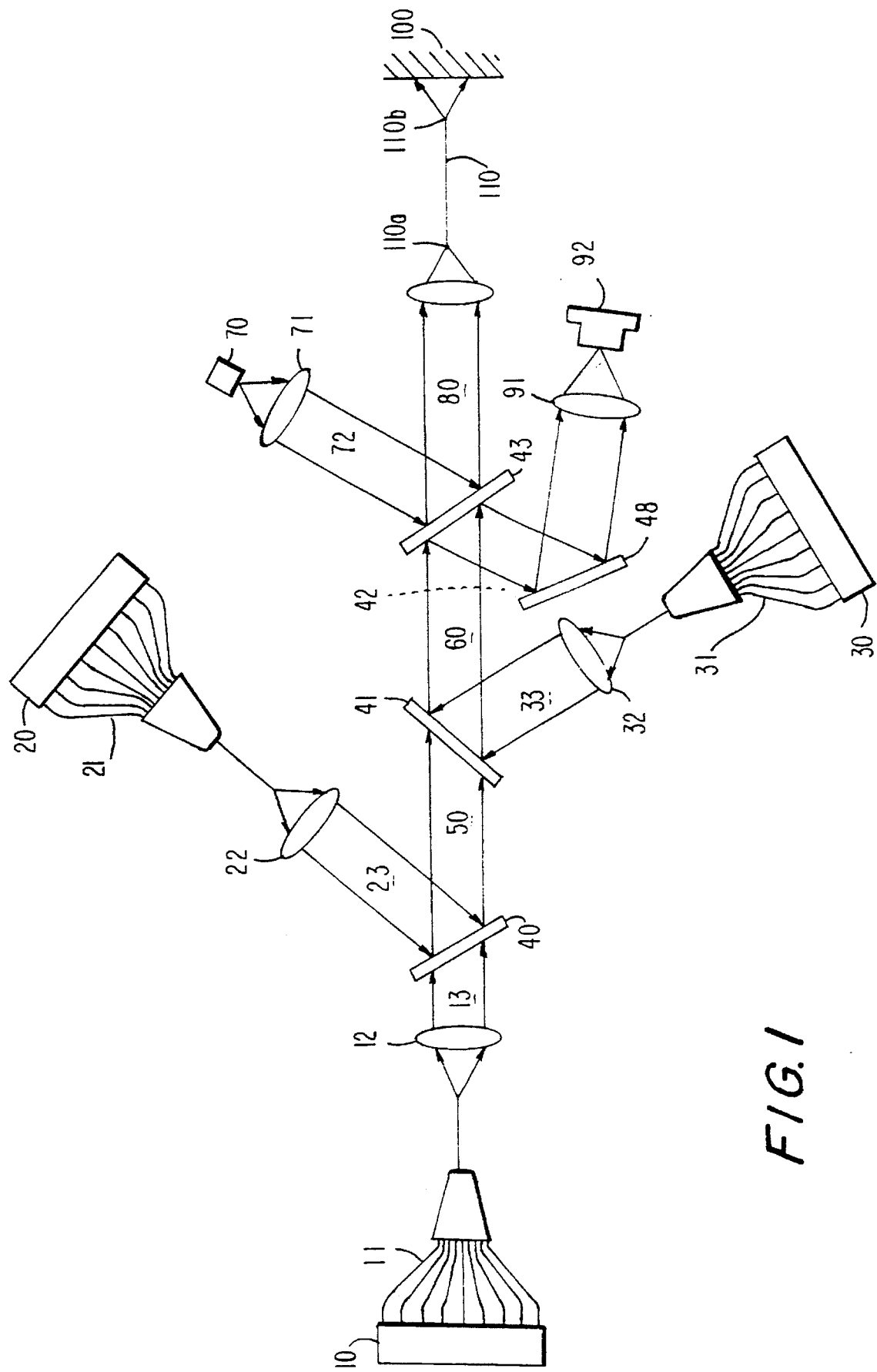
FIG. 1 illustrates one form of apparatus constructed in accordance with the present invention.

FIG. 1 depicts a bright light source in accordance with the invention such that the laser beam from the source is applied onto a working surface, such as tissue to be subjected to a medical laser treatment. The input power of each light source, as defined by a plurality of laser diodes, is of the order of many watts or tens of watts. The produced composite beam is transmitted a relatively short distance (e.g., up to a few meters) such that the losses are very low or negligible, and therefore, the power of the composite beam is substantially equal to the sum of the powers of the input beams, again many watts or tens of watts.

The above technique for producing a bright light source is applicable generally with respect to a wide variety of light sources, but is particularly attractive in the case of laser diodes. It is known that laser diodes are small, efficient, easy to drive and modulate, very reliable, and of relatively low cost. However, the brightness of the presently known laser diodes, including the high power laser diodes, is generally far below the brightness of gas lasers or solid state lasers. Thus, the resulting power per unit area, per unit solid angle of laser light radiation generated by a laser diode, is insufficient for many medical laser applications.

The present invention exploits the above advantageous characteristics of laser diodes, and the further characteristic that laser diodes can be made to lase in a wide range of wavelengths. For example, the presently known high power laser diodes made of GaAlAs emit light in a range of 780 to 880 nm, and diodes made of InGaAs emit light in the range of 920 to 980 nm. The above-described techniques for increasing the brightness of a beam of light thus enables laser diodes to be used in applications, such as in medical laser applications, requiring high brightness outputs.

Thus, in the preferred embodiment of the invention, the source beam generators include a plurality of laser diodes of different wavelengths. In the described example, these generators include a first plurality of diodes 10 that produce laser beams of 780 nm, a second plurality of laser diodes 20 that produce laser beams of 860 nm, and a third plurality of laser diodes 30 that produce laser beams of 960 nm. It will be obvious to one skilled in the art that the generators could also be single high powered laser diodes of the previously mentioned frequencies. The power of each laser beam formed by combining the first plurality of laser diodes, the second plurality of laser diodes and the third plurality of laser diodes respectively is at least 10 watts, preferably about 15 watts. Thus the power of the composite output beam is approximately 45 watts, sufficient for use in many surgical laser applications. It will be appreciated that if higher powers are desired, more than three source beams can be combined in accordance with the present invention.

According to further features of the preferred embodiment, the plurality of beams are combined into the single composite beam such that the product of the cross-sectional area and the solid angle, of the single composite beam is substantially the same as the product in each of the source beams.

The apparatus illustrated in the drawing includes a first plurality of laser diodes 10, a second plurality of laser diodes 20 and a third plurality of laser diodes 30 generating laser beams of different wavelengths, e.g., of 780, 860 and 960 nm, respectively. As the laser energy from each plurality of laser diodes is emitted from a relatively wide area (typically about 10 mm), the output from each plurality of laser diodes is directed to a fibre bundle 11, 21 and 31 respectively, which is tightly packed at the output end, e.g., to a circle of about 1 mm in diameter. Lenses 12, 22 and 32, respectively, collimate the light from each fibre bundle to produce three essentially collimated beams 13, 23 and 33, respectively.

The illustrated apparatus further includes frequency responsive optics in the form of a plurality of wavelength combiners 40, 41 for combining the plurality of light beams 13, 23 and 33, respectively, into a single composite beam. Thus, a first combiner 40 combines beams 13 and 23 into a composite beam 50; and a second combiner 41 combines beams 50 and 33 into a single composite beam 60.

In the illustrated example, combiners 40 and 41 are both dichroic elements, e.g., interference filters, which are highly transparent to one wavelength band and highly reflective to the other wavelength band. Thus, dichroic combiner 40 is highly transmissive with respect to the wavelength of laser beam 13 and is highly reflective with respect to the wavelength of laser beam 23; whereas combiner 41 is highly transmissive with respect to the wavelengths of both laser beams 13 and 23, and is highly reflective with respect to the wavelength of laser beam 33.

Each of the plurality of laser diodes 10, 20 and 30, should output at least one watt of power, preferably at least 10 watts of power in medical laser applications of the invention. In the illustrated example, each outputs 15 watts of power, so that the power of the single composite beam 60 is approximately 45 watts. This is normally sufficient to permit the laser beam to be used for many medical laser applications.

The illustrated apparatus further includes a safety shutter 42 in the path of the single composite beam 60, in order to selectively block the transmission of the single composite beam to the working surface 100.

The illustrated system further includes a fourth laser 70 which generates a laser beam of visible light and of low power, to serve as a visible aiming beam to be projected onto the working surface 100 in order to permit aiming the high powered composite beam 60. In the illustrated example, the aiming beam laser 70 is a laser diode generating a laser beam of 635 nm wavelength and of a few milliwatts of power. This laser beam is collimated by a lens 71 to produce a collimated beam 72 which is combined by a third dichroic combiner 43 with the high power composite beam 60 from the three pluralities of laser diodes 10, 20 and 30. Dichroic combiner 43 would thus be highly transmissive with respect to the wavelengths of the three pluralities of laser diodes 10, 20 and 30 but highly reflective with respect to the wavelength of the aiming laser 70. The output of the dichroic combiner 43 is thus a single composite beam 80 including the outputs of the three pluralities of laser diodes 10, 20 and 30 and the output of the aiming beam laser 70.

The output 80 of dichroic combiner 43 is then directed, via a focusing lens 90, into the inlet end 110a of a guiding optical fibre 110. The single composite beam exits from the outlet end 110b of the optical fibre 110 onto the working surface 100.

In the described apparatus, the combiners 40, 41 and 43, as well as the optics of the apparatus, are such that the product of the cross-sectional area and the solid angle of the single composite beam 80 outputted by combiner 43 is substantially the same as in each of the beams exiting from the plurality of laser diodes 10, 20 and 30 via their respective bundles.

Thus, the outlet end 110b of the guiding optical fibre 110 becomes a light source of high brightness, almost three times that of each of the pluralities of laser diodes, thereby enabling the use of laser sources, particularly laser diodes, for applications requiring high power and high brightness, such as medical laser applications.

While the dichroic combiner 43 is highly transmissive of the wavelengths of the three essentially collimated beams 13, 23 and 33 in the composite beam 60, a small fraction of the energy in the composite beam is reflected by the combiner 43. This small fraction reflected by combiner 43 is used for monitoring the power produced in the composite beam 80. For this purpose, the small fraction of the laser power reflected by combiner 43 is reflected by a mirror 44 through a focusing lens 91 onto a power detector 92 for measuring the laser energy so reflected from the combiner 43. Since the proportion of laser energy reflected by combiner 43 to the laser energy passing through the combiner 43 is known, depending on the characteristics of the combiner, the output of power detector 92 also provides a measurement of the total energy in the composite beam 80 applied, via optical fibre 110, onto the working surface 100.

It will be appreciated that whereas the illustrated system includes dichroic combiners, other types of wavelength combiners may be used for multiplexing the laser beams, e.g., a holographic element or grating, as known in the prior art. It will also be appreciated that whereas the illustrated apparatus shows combining three light sources, namely plurality of laser diodes 10, 20 and 30 together with the aiming beam laser 70, only two, or more than three, light sources could be combined, according to the requirements of a particular application.

It will thus be seen that the invention efficiently attains the objects set forth above, among those made apparent from the preceding description. In particular, the invention provides a method of and an apparatus for generating bright light sources using semiconductor lasers of different frequencies to perform medical laser applications. Those skilled in the art will appreciate that the configuration depicted in FIG. 1 efficiently and effectively attains a bright light source having a high power emitted from a tight radius into a confined solid angle.

It will be understood that changes may be made in the above construction and in the foregoing sequences of operation without departing from the scope of the invention. For instance it will be appreciated that the invention could be advantageously used in other applications requiring bright light sources, e.g., metal welding. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A method of performing a medical laser application including the steps of:

generating a first laser beam of a first frequency;

generating a second laser beam of a second frequency;

said first and second laser beams being generated by diode lasers;

said first frequency and said second frequency being different frequencies that are differentiatable by frequency responsive optics but close enough in frequency to have the same effect on tissue;

combining said first and second laser beams into a composite laser beam using frequency responsive optics; and shining said composite laser beam into tissue to perform said medical laser application.

2. The method according to claim 1, further including the steps of:

generating a third laser beam of a third frequency;

said third frequency being different from said first frequency and from said second frequency with respect to frequency responsive optics but being close enough in frequency to said first frequency and said second frequency to have the same effect on tissue;

combining said third laser beam with said first and second laser beams into said composite laser beam.

3. The method according to claim 2, wherein:

said third laser beam is generated by diode lasers.

4. The method according to claim 2 wherein said first laser beam is of a wavelength of 780 nm and of a power of at least 10 watts;

said second laser beam is of a wavelength of 860 nm and of a power of at least 10 watts; and said third laser beam is of a wavelength of 960 nm and of a power of at least 10 watts.

5. The method according to claim 1 or 2, wherein at least said first laser beam, said second laser beam and said composite laser beam each has a cross-sectional area and a solid angle such that the product of the cross-sectional area and the solid angle of the composite laser beam is substantially the same as that of each of said first and second laser beams.

6. The method according to claim 1 or 2 wherein at least said first and second laser beams are combined into said composite beam by a dichroic combiner.

7. The method according to claim 1 or 2 wherein at least said first and second laser beams are combined into said composite beam by a holographic element.

8. The method according to claim 1 or 2 wherein at least said first and second laser beams are combined into said composite beam by a grating.

9. The method according to claim 1 or 2 wherein said diode lasers are at least one watt of power each.

10. The method according to claim 1 or 2 wherein a small fraction of the composite beam is split-off and is directed to a power detector for measuring the power of said composite beam.

11. The method according to claim 1 or 2 wherein an aiming beam of visible light and of a different wavelength than said first and second laser beams is also generated and combined into said composite beam.

12. The method according to claim 11, wherein said aiming beam is of a wavelength of 635 nm and of a power of a few milliwatts.

13. The method according to claim 1 or 2 wherein said composite beam is directed into said tissue by an optical fibre.

14. A bright light source including:

a first plurality of semiconductor lasers in which each of said first plurality of semiconductor lasers emits a beam of light of a first frequency;

a second plurality of semiconductor lasers in which each of said second plurality of semiconductor lasers emits a beam of light of a second frequency;

said first frequency and said second frequency being different frequencies that are differentiatable by frequency responsive optics but close enough in frequency to have the same effect on tissue;

a first bundle of optical fibers for receiving the light from ones of said first plurality of semiconductor lasers and providing a first combined laser beam of a predetermined shape and having a cross-sectional area and a solid angle;

a second bundle of optical fibers for receiving the light from ones of said second plurality of semiconductor lasers and providing a second combined laser beam of a predetermined shape and having a cross-sectional area and a solid angle; and frequency responsive optics for combining said first and second combined laser beams into a composite laser beam, said composite laser beam having substantially the same product of cross-sectional area and solid angle as each of said first and second combined beams.

15. A bright light source as defined in claim 14 wherein said first plurality of semiconductor lasers are arranged in a first monolithic array; and said second plurality of semiconductor lasers are arranged in a second monolithic array.

16. A bright light source as defined in claim 14 further including:
- a third plurality of semiconductor lasers in which each of said third plurality of semiconductor lasers emits a beam of light of a third frequency;
- said third frequency being different from said first frequency and from said second frequency with respect to frequency responsive optics but being close enough in frequency to said first frequency and said second frequency to have the same effect on tissue;
- a third bundle of optical fibers for receiving the light from ones of said third plurality of semiconductor lasers and providing a third combined laser beam of a predetermined shape and having a cross-sectional area and a solid angle.

17. The apparatus according to any one of claims 14–16, wherein
said semiconductor lasers are high power diode lasers.

18. The apparatus according to any one of claims 14–16, wherein
said frequency responsive optics include a dichroic combiner.

19. The apparatus according to any one of claims 14–16, wherein
said frequency responsive optics include a grating.

20. The apparatus according to any one of claims 14–16, wherein
said frequency responsive optics include a holographic element.

21. The apparatus according to any one of claims 14–16, further including
a power detector for receiving a small fraction of the composite beam and for measuring the power of the combined beam.

22. The apparatus according to any one of claims 14–16, wherein
each of said combined beams is at least 10 watts of power.

23. The apparatus according to any one of claims 14–16, wherein
said first plurality of semiconductor lasers each generates a laser beam of between 780 nm and 880 nm inclusive; and
said second plurality of semiconductor lasers each generates a laser beam of between 920 nm and 940 nm inclusive.

24. The apparatus according to any one of claims 14–16, including
a light source for generating an aiming beam of visible light and of a different wavelength than said plurality of semiconductor lasers; and
a multiplexer for multiplexing said aiming beam into said combined laser beam.

25. The apparatus according to claim 24, wherein said further light source generates an aiming beam of 635 nm and of a few milliwatts of power.

* * * * *